(12) United States Patent
Brenner et al.

(10) Patent No.: US 7,579,153 B2
(45) Date of Patent: *Aug. 25, 2009

(54) ISOTHERMAL DNA AMPLIFICATION

(75) Inventors: Sydney Brenner, Ely (GB); Gi Mikawa, Cambridge (GB)

(73) Assignee: Population Genetics Technologies, Ltd., Cambridge (GB)

(*) Notice: Subject to any disclaimer, the term of this patent is extended or adjusted under 35 U.S.C. 154(b) by 299 days.

This patent is subject to a terminal disclaimer.

(21) Appl. No.: 11/338,533

(22) Filed: Jan. 23, 2006

(65) Prior Publication Data

US 2006/0166250 A1 Jul. 27, 2006

Related U.S. Application Data

(60) Provisional application No. 60/647,064, filed on Jan. 25, 2005.

(51) Int. Cl.
*C12Q 1/68* (2006.01)

(52) U.S. Cl. .......................... 435/6; 435/91.1; 435/91.2

(58) Field of Classification Search .................. None
See application file for complete search history.

(56) References Cited

U.S. PATENT DOCUMENTS

| | | | |
|---|---|---|---|
| 5,130,238 A | 7/1992 | Malek | 435/91 |
| 5,169,766 A | 12/1992 | Schuster | 435/91 |
| 5,194,370 A | 3/1993 | Berninger | 435/6 |
| 5,215,899 A | 6/1993 | Dattagupta | 435/6 |
| 5,399,491 A | 3/1995 | Kacian | 435/91.21 |
| 5,409,818 A | 4/1995 | Davey | 435/91.21 |
| 5,437,990 A | 8/1995 | Burg | 435/91.2 |
| 5,474,916 A | 12/1995 | Reischl | 435/91.2 |
| 5,545,522 A | 8/1996 | Van Gelder | 435/6 |
| 5,616,478 A | 4/1997 | Chetverin | 435/91.2 |
| 5,766,849 A | 6/1998 | McDonough | 435/6 |
| 5,891,636 A | 4/1999 | Van Gelder | 435/6 |
| 5,914,229 A | 6/1999 | Loewy | 435/6 |
| 5,932,451 A | 8/1999 | Wang | 435/91.21 |
| 6,025,133 A | 2/2000 | Stull | 435/6 |
| 6,132,997 A | 10/2000 | Shannon | 435/91.21 |
| 6,379,899 B1 | 4/2002 | Ullman | 435/6 |
| 6,403,319 B1 | 6/2002 | Lizardi | 435/6 |
| 6,511,803 B1 | 1/2003 | Church et al. | 435/6 |
| 6,686,156 B2 | 2/2004 | Kurn | 435/6 |
| 6,787,308 B2 | 9/2004 | Balasubramanian | |
| 6,794,141 B2 | 9/2004 | Erlander | 435/6 |
| 2003/0165963 A1 | 9/2003 | Dattagupta | 435/6 |
| 2003/0219792 A1 | 11/2003 | Armes et al. | 435/6 |
| 2004/0058378 A1* | 3/2004 | Kong et al. | 435/6 |
| 2004/0161792 A1 | 8/2004 | Liao | 435/6 |
| 2005/0112631 A1 | 5/2005 | Piepenburg | 435/6 |
| 2005/0142559 A1 | 6/2005 | Makrigiorgos | 435/6 |
| 2007/0031857 A1* | 2/2007 | Makarov et al. | 435/6 |

FOREIGN PATENT DOCUMENTS

| | | |
|---|---|---|
| WO | WO 2004/027025 | 4/2004 |
| WO | WO 2004/076683 | 9/2004 |

OTHER PUBLICATIONS

Kim et al, "DARFA: A novel technique for studying differential gene expression and bacterial comparative genomics," Biochemical and Biophysical Research Communications, 336: 168-174 (2005).
Kwok et al, "Transcription-based amplification system and detection of amplified human immunodeficiency virus type I with a bead-based sandwich hybridization format," Proc. Natl. Acad. Sci., 86: 1173-1177 (1989).
Guatelli et al, "Isothermal, in vitro amplification of nucleic acids by a multienzyme reaction modeled after retroviral replication," Proc. Natl. Acad. Sci., 87: 1874-1878 (1990).

* cited by examiner

*Primary Examiner*—Gary Benzion
*Assistant Examiner*—Heather G Calamita
(74) *Attorney, Agent, or Firm*—Bozicevic, Field & Francis, LLP; David C. Scherer

(57) ABSTRACT

The present invention provides for amplification of one or more polynucleotides by multi-staged linear amplifications using one or more RNA polymerases. At each stage RNA transcripts are accumulated at a linear rate, so that multiple stages provide for faster than linear transcript accumulation. In one aspect, the invention provides for polynucleotide amplification by ligating hairpin adaptors to an end of polynucleotides wherein the hairpin adaptors each contain a promoter sequence oriented so that transcription proceeds in the direction of the loop of the hairpin adaptor. Upon transcription through such loop region and to the complementary strand a replicate is made of the promoter sequence as well as the polynucleotide, thereby permitting exponential amplification upon reverse transcription, second strand synthesis, and repetition of the above cycle. Preferably such amplification is carried out under isothermal reaction conditions.

16 Claims, 10 Drawing Sheets

Input DNA (100)(SEQ ID NO: 1)

5'-GCTAATACGACTCACTATAGGGATTCTATCCCAATTAACCCTCACTAAAGGGAGACCATGGTCTTGCTAGCCTTGAACCGTCGATTGGCTT
CGATTATGCTGAGTGATATCCCTAAGATAGGGTTAATTGGGAGTGATTCCCTCTGGTACCAGAACGATCGGAACTTGGCAGCTAACCGAA

| T7 promoter | Stem-Loop | T3 promoter | NcoI | NheI | Tag | Cap |

T7 Transcript (102)(SEQ ID NO: 2)

5'-GGGAUUCUAUCCCAAUUAACCCUCACUAAAGGGAGACCAUGGUCUUGCUAGCCUUGAACCGUCGAUUGGCUU

First Strand cDNA and Self Priming 3' End (104)(SEQ ID NO: 3)

5'-GGGAUUCUAUCCCAAUUAACCCUCACUAAAGGGAGACCAUGGUCUUGCUAGCCUUGAACCGUCGAUUGGCUU

3'-CCCTAAGATAGGGTTAATTGGGAGTGATTCCCTCTGGTACCAGAACGATCGGAACTTGGCAGCTAACCGAA

105

Reconstitution of Active T3 Promoter (106)(SEQ ID NO: 4)

G AATCCCAATTAACCCTCACTAAAGGGAGACCATGGTCTTGCTAGCCTTGAACCGTCGATTGGCTT-3'
G ATAGGGTTAATTGGGAGTGATTCCCTCTGGTACCAGAACGATCGGAACTTGGCAGCTAACCGAA-5'

Fig. 1

ISOTHERMAL DNA AMPLIFICATION

This application claims priority to U.S. provisional application Ser. No. 60/647,064 filed 25 Jan. 2005, which application is incorporated by reference.

FIELD OF THE INVENTION

The present invention relates to methods for amplifying polynucleotides, and more particularly, for amplifying on a solid phase support a single strand of a double stranded target DNA.

BACKGROUND

Much of the progress in genetics and biotechnology has depended on the availability of techniques for amplifying nucleic acids to produce amounts amenable for analysis, for example, by sequencing, hybridization, fluorescent labeling, or the like. A wide variety of amplification techniques have been developed for this purpose, including polymerase chain reaction (PCR), ligase chain reaction (LCR), nucleic acid sequence-based amplification (NASBA), rolling circle, and the like.

PCR has been the most widely used method to amplify DNA from small quantities of DNA molecules. Although it is efficient and generates large quantities of DNA from small aliquots of DNA template, PCR always introduces biases when it is applied to amplify complex DNA libraries. A host of factors affect the relative amplification rates of individual sequences with a library, including the preference of primer annealing sites, the length and GC content differences of the template DNAs, non-specific priming at interior sites of sequences, temporal differences in extension times, and the like. Frequently, because of such factors, the polymerization, or primer extension, step is terminated prematurely by the denaturation step of the PCR; hence, smaller fragments and low GC content fragments are preferentially amplified.

It would be very useful for many applications where nucleic amplification plays a key role, if an amplification technique were available that minimized or eliminated the above short-comings of PCR.

SUMMARY OF THE INVENTION

The present invention provides for amplification of one or more polynucleotides by multi-staged linear amplifications using one or more RNA polymerases. At each stage RNA transcripts are accumulated at a linear rate, so that multiple stages provide for faster than linear transcript accumulation. RNA transcripts at each stage are converted back into DNA to permit further production of secondary, tertiary, or higher order RNA transcripts, depending on the embodiment. In one aspect, the invention provides two stages of RNA transcript production, preferably under isothermal reaction conditions.

In one aspect, the invention is implemented by the method comprising the following steps: (i) providing a double stranded DNA having a hairpin at one end, the polynucleotide at the other end, and disposed therebetween a promoter sequence oriented so that synthesis by an RNA polymerase recognizing the promoter sequence proceeds in the direction of the hairpin; (ii) transcribing the double stranded DNA with an RNA polymerase that recognizes the promoter sequence to form an RNA transcript comprising copies of the promoter sequence and the polynucleotide; (iii) generating a complementary DNA from the RNA transcript; (iv) displacing a 5' end of the RNA transcript from the complementary DNA so that the hairpin is reconstituted; and (v) extending the hairpin to generate the double stranded DNA containing a reconstituted promoter sequence, the RNA polymerase recognizing the reconstituted promoter sequence and synthesizing RNA transcripts. In a preferred embodiment, the step of generating includes forming a heteroduplex of said complementary DNA and said RNA transcript and wherein said step of displacing includes treating the heteroduplex with a helicase.

In another aspect, the invention provides a method of amplifying a polynucleotide comprising the following steps: (i) providing a single stranded DNA containing a promoter sequence and a polynucleotide, the single stranded DNA having a 5' end, a 3' end, and complementary sequences at the 3' end capable of forming a hairpin having a loop region and a duplex region, the promoter sequence being disposed between the polynucleotide and the 3' end and the single stranded the single stranded DNA being attached to a solid phase support by its 5' end; (ii) extending the duplex to form a double stranded DNA that includes the polynucleotide and complement thereof and the promoter sequence and complement thereof, thereby forming an operational promoter; and (iii) generating RNA copies of the polynucleotide with an RNA polymerase that recognizes the operational promoter.

In another aspect, the above step of providing further includes providing a double strand DNA that contains in series an up-stream promoter, a first stem region, said loop region and complement thereof, a second stem region, said polynucleotide, and a primer binding site, wherein RNA copies of a strand of the double stranded DNA are generated by treating under synthesis conditions the double stranded DNA with an RNA polymerase that recognized the up-stream promoter, and wherein the RNA copies of a strand of the double stranded DNA are captured by specific hybridization of the primer binding site to a complement thereof attached to a solid phase support.

The invention further includes kits and compositions for carrying out the method of the invention. In one aspect, such kits include a composition of one or more hairpin adaptors that each contains a loop region and a double stranded region, wherein the double stranded region contains a promoter site oriented so that synthesis takes place in the direction of the loop region. In another aspect, such kits further include at least one RNA polymerases, at least one reverse transcriptases, and at least one primer (e.g. first primer), and appropriate buffers for implementing the method of the invention. In another aspect, such kits further include at least one DNA polymerase and at least one helicase and appropriate buffers for implementing the method of the invention.

The invention provides a method and compositions for polynucleotide amplification that minimizes amplification biases that are found in PCR. A priming step is eliminated in the second stranded DNA synthesis reaction by employing self-priming with the formation of an intramolecular looped structure at the 3' terminus of the first stranded DNA; thus, the priming is accurate and faster than intermolecular priming.

BRIEF DESCRIPTION OF THE FIGURES

FIG. 1 lists nucleotide sequences related to an example of the invention.

DEFINITIONS

Figure 2A:
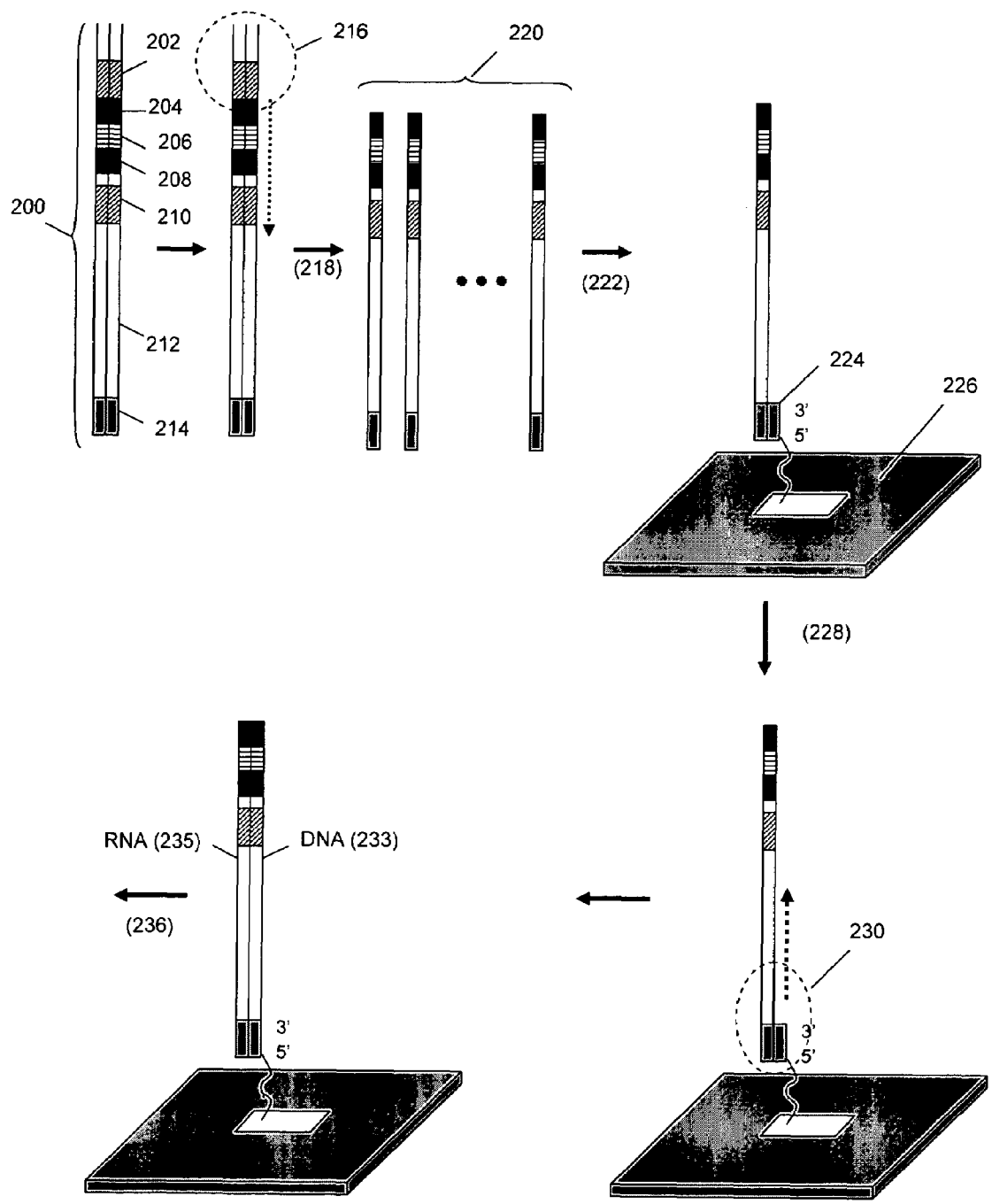
FIGS. 2A-2D diagrammatically illustrate steps of several embodiments of the invention.

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

"Addressable" in reference to tag complements means that the nucleotide sequence, or perhaps other physical or chemical characteristics, of an end-attached probe, such as a tag complement, can be determined from its address, i.e. a one-to-one correspondence between the sequence or other property of the end-attached probe and a spatial location on, or characteristic of, the solid phase support to which it is attached. Preferably, an address of a tag complement is a spatial location, e.g. the planar coordinates of a particular region containing copies of the end-attached probe. However, end-attached probes may be addressed in other ways too, e.g. by microparticle size, shape, color, frequency of micro-transponder, or the like, e.g. Chandler et al, PCT publication WO 97/14028.

"Allele frequency" in reference to a genetic locus means the frequency of occurrence within a population of a particular nucleotide or sequence segment, or other sequence marker, such as an insertion or deletion of one or more nucleotides, or a particular sequence motif, at or within the genetic locus. In reference to the above, a population may be a population of individual from a defined group, e.g. Caucasian women over the age of 50, or a population may be a population of cells from an individual suffering from a disease or condition, such as cancer. In some contexts, an allele frequency may also refer to the frequency of sequences not identical to, or exactly complementary to, a reference sequence, or a set of reference sequences.

"Amplicon" means the product of a polynucleotide amplification reaction. That is, it is a population of polynucleotides, usually but not necessarily double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like. "RNA amplicon" means an amplicon of RNA molecules; that is, starting sequences, which may be RNA or DNA, give rise to RNA replicates in an amplicon.

"Complementary or substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick base pairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Genetic locus," or "locus" in reference to a genome or target polynucleotide, means a contiguous subregion or segment of the genome or target polynucleotide. As used herein, genetic locus, or locus, may refer to the position of a gene or portion of a gene in a genome, or it may refer to any contiguous portion of genomic sequence whether or not it is within, or associated with, a gene. Preferably, a genetic locus refers to any portion of genomic sequence from a few tens of nucleotides, e.g. 10-30, or 10-100, in length, to a few hundred nucleotides, e.g. 100-1000 or 100-500 in length, to a few thousands of nucleotide in length, e.g. 1000-10,000 or 1000-3000 in length. In some contexts, genetic locus may refer to the location of a nucleotide within a genome.

"Kit" refers to any delivery system for delivering materials or reagents for carrying out a method of the invention. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents arid/or supporting materials. Such contents may be delivered to the intended recipient together or separately. For example, a first container may contain an enzyme for use in an assay, while a second container contains probes.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whitely et al, U.S. Pat. No. 4,883,750; Letsinger et al, U.S. Pat. No. 5,476, 930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al, Methods in Enzymology, 68: 50-71 (1979); Engler et al, The Enzymes, 15: 3-29 (1982); and Namsaraev, U.S. patent publication 2004/0110213.

"Microarray" refers to a solid phase support having a planar surface, which carries an array of nucleic acids, each member of the array comprising identical copies of an oligonucleotide or polynucleotide immobilized to a spatially defined region or site, which does not overlap with those of other members of the array; that is, the regions or sites are spatially discrete. Spatially defined hybridization sites may additionally be "addressable" in that its location and the identity of its immobilized oligonucleotide are known or predetermined, for example, prior to its use. Typically, the oligonucleotides or polynucleotides are single stranded and are covalently attached to the solid phase support, usually by a 5'-end or a 3'-end. The density of non-overlapping regions containing nucleic acids in a microarray is typically greater than 100 per cm$^2$, and more preferably, greater than 1000 per cm$^2$. Microarray technology is disclosed in the following references that are incorporated by reference: Schena, Editor, Microarrays: A Practical Approach (IRL Press, Oxford, 2000); Southern, Current Opin. Chem. Biol., 2: 404-410 (1998); Nature Genetics Supplement, 21: 1-60 (1999). The synthesis of high-density microarrays is disclosed in the following exemplary references that are incorporated by reference: Fodor et al, U.S. Pat. Nos. 5,424,186; 5,744,305; 5,445, 934; 6,355,432; 6,440,667 (Affymetrix, Santa Clara, Calif.); Cerrina et al, U.S. Pat. No. 6,375,903 (NimbleGen, Madison, Wis.); and "ink-jet" synthesized microarrays, e.g. disclosed in Hughes et al, Nature Biotechnology, 19: 342-347 (2001); Caren et al U.S. Pat. No. 6,323,043 (Agilent Technologies, Palo Alto, Calif.); and the like. As used herein, "random microarray" refers to a microarray whose spatially discrete regions of oligonucleotides or polynucleotides are not spatially addressed. That is, the identity of the attached oligonucleoties or polynucleotides is not discernable, at least initially, from its location. In one aspect, random microarrays are planar arrays of microbeads wherein each microbead has attached a single kind of hybridization tag complement, such as from a minimally cross-hybridizing set of oligonucleotides. Arrays of microbeads may be formed in a variety of ways, e.g. Brenner et al, Nature Biotechnology, 18: 630-634 (2000); Tulley et al, U.S. Pat. No. 6,133,043; Stuelpnagel et al, U.S. Pat. No. 6,396,995; Chee et al, U.S. Pat. No. 6,544, 732; and the like. Likewise, after formation, microbeads, or oligonucleotides thereof, in a random array may be identified in a variety of ways, including by optical labels, e.g. fluorescent dye ratios or quantum dots, shape, sequence analysis, or the like. Hybridization conditions typically include salt concentrations of less than about 1M, more usually less than about 500 mM and less than about 200 mM. Hybridization temperatures can be as low as 5° C., but are typically greater than 22° C., more typically greater than about 30° C., and preferably in excess of about 37° C. Hybridizations are usually performed under stringent conditions, i.e. conditions under which a probe will stably hybridize to a perfectly complementary target sequence, but will not stably hybridize to sequences that have one or more mismatches. The stringency of hybridization conditions depends on several factors, such as probe sequence, probe length, temperature, salt concentration, concentration of organic solvents, such as formamide, and the like. How such factors are selected is usually a matter of design choice to one of ordinary skill in the art for any particular embodiment. Usually, stringent conditions are selected to be about 5° C. lower than the $T_m$ for the specific sequence for particular ionic strength and pH. Exemplary hybridization conditions include salt concentration of at least 0.01 M to no more than 1 M Na ion concentration (or other salts) at a pH 7.0 to 8.3 and a temperature of at least 25° C. Additional exemplary hybridization conditions include the following: 5× SSPE (750 mM NaCl, 50 mM sodium phosphate, 5 mM EDTA, pH 7.4). Exemplary hybridization procedures for applying labeled target sequence to a GenFlex™ microarray (Affymetrix, Santa Clara, Calif.) is as follows: denatured labeled target sequence at 95-100° C. for 10 minutes and snap cool on ice for 2-5 minutes. The microarray is pre-hybridized with 6× SSPE-T (0.9 M NaCl 60 mM NaH$_2$, PO$_4$, 6 mM EDTA (pH 7.4), 0.005% Triton X-100)+0.5 mg/ml of BSA for a few minutes, then hybridized with 120 µL hybridization solution (as described below) at 42° C. for 2 hours on a rotisserie, at 40 RPM. Hybridization Solution consists of 3M TMACL (Tetramethylammonium. Chloride), 50 mM MES ((2-[N-Morpholino]ethanesulfonic acid) Sodium Salt) (pH 6.7), 0.01% of Triton X-100, 0.1 mg/ml of Herring Sperm DNA, optionally 50 pM of fluorescein-labeled control oligonucleotide, 0.5 mg/ml of BSA (Sigma) and labeled target sequences in a total reaction volume of about 120 µL. The microarray is rinsed twice with 1× SSPE-T for about 10 seconds at room temperature, then washed with 1× SSPE-T for 15-20 minutes at 40° C. on a rotisserie, at 40 RPM. The microarray is then washed 10 times with 6× SSPE-T at 22° C. on a fluidic station (e.g. model FS400, Affymetrix, Santa Clara, Calif.). Further processing steps may be required depending on the nature of the label(s) employed, e.g. direct or indirect. Microarrays containing labeled target sequences may be scanned on a confocal scanner (such as available commercially from Affymetrix) with a resolution of 60-70 pixels per feature and filters and other settings as appropriate for the labels employed. GeneChip Software (Affymetrix) may be used to convert the image files into digitized files for further data analysis.

"Mismatch" means a base pair between any two of the bases A, T (or U for RNA), G, and C other than the Watson-Crick base pairs G-C and A-T. The eight possible mismatches are A-A, T-T, G-G, C-C, T-G, C-A, T-C, and A-G.

"Mutation" and "polymorphism" are usually used somewhat interchangeably to mean a DNA molecule, such as a gene that differs in nucleotide sequence from a reference DNA sequence or wild type sequence, or normal tissue sequence, by one or more bases, insertions, and/or deletions. In some contexts, the usage of Cotton (Mutation Detection, Oxford University Press, Oxford, 1997) is followed in that a mutation is understood to be any base change whether pathological to an organism or not, whereas a polymorphism is usually understood to be a base change with no direct pathological consequences.

"Nucleoside" as used herein includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having, modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al, Exp. Opin. Ther. Patents, 6: 855-870 (1996); Mesmaeker et al, Current Opinion in Structual Biology, 5: 343-355 (1995); and the like. Exemplary types of polynucleotides that are capable of enhancing duplex stability include oligonucleotide N3'→P5' phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids (LNAs), and like compounds. Such oligonucleotides are either available commercially or may be synthesized using methods described in the literature.

"Perfectly matched" in reference to a duplex means that the poly- or oligonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. In reference to a triplex, the term means that the triplex consists of a perfectly matched duplex and a third strand in which every nucleotide undergoes Hoogsteen or reverse Hoogsteen association with a basepair of the perfectly matched duplex. Conversely, a "mismatch" in a duplex between a tag and an oligonucleotide means that a pair or triplet of nucleotides in the duplex or triplex fails to undergo Watson-Crick and/or Hoogsteen and/or reverse Hoogsteen bonding.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred μL, e.g. 200 μL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999)(two-color real-time PCR). Usually, distinct sets of primers are employed for each sequence being amplified. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

"Polynucleotide" or "oligonucleotide" are used interchangeably and each mean a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moities, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, $2^{nd}$ Edition (Cold Spring Harbor Press, New York, 2003).

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the address and fluorescence intensity of a signal being generated at each hybridization site of the microarray; thus, such a readout may be registered or stored in various ways, for example, as an image of the microarray, as a table of numbers, or the like. A readout is "digital" when the number or value is obtained by a counting process, e.g. determining a value by counting on a microarray the number of hybridization from which signals are being generated (as distinguished from those sites not generating signals).

"Sample" means a quantity of material from a biological, environmental, medical, or patient source in which detection or measurement of target nucleic acids is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

"Solid support", "support", and "solid phase support" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. Microarrays usually comprise at least one planar solid phase support, such as a glass microscope slide.

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

As used herein, the term "$T_m$" is used in reference to the "melting temperature." The melting temperature is the temperature at which a population of double-stranded nucleic acid molecules becomes half dissociated into single strands. Several equations for calculating the Tm of nucleic acids are well known in the art. As indicated by standard references, a simple estimate of the Tm value may be calculated by the equation. Tm=81.5+0.41 (% G+C), when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr., Biochemistry 36, 10581-94 (1997)) include alternative methods of computation which take structural and environmental, as well as sequence characteristics into account for the calculation of Tm.

"Vector" or "cloning vector" refers to an extrachromosomal genetic element which can be used to replicate a DNA fragment in a host organism. A wide variety of cloning vectors are commercially available for use with the invention, e.g. New England Biolabs (Beverely, Mass.); Stratagene Cloning Systems (La Jolla, Calif.); Clontech Laboratories (Palo Alto, Calif.); and the like. Usually, cloning vectors used with the invention are bacterial plasmids.

DETAILED DESCRIPTION OF THE INVENTION

The invention provides a method for amplifying, or replicating, one or more polynucleotides in a reaction. In one aspect, the method converts a strand of a DNA duplex into an RNA amplicon in a multi-stage reaction that exponentially increases the number of replicate molecules with time. In accordance with the invention, replication in each stage of the reaction is accomplished by providing a promoter site in an operational configuration with the polynucleotide to be amplified, or a replicate of it. Thus, at each stage, each replicate is linearly-amplified for a combined amplification rate across all the reaction stages that is greater than linear. In another aspect, the methods of the invention are carried out under isothermal reaction conditions. In still another aspect, methods of the invention can be implemented on a solid phase support to create amplicons containing a single kind of molecule, which amplicons are restricted to discrete locations on a surface of such solid phase support, e.g., as illustrated below, by hybridizing to complementary oligonucleotides attached to the surface at such discrete locations. Below, exemplary embodiments are described that implement the principles of the invention. In a first embodiment, a two-stage reaction is described in which two different promoters, each recognized by a different RNA polymerase, are used in a different stage of an overall reaction. In a second embodiment, a two-stage reaction is described in which a single promoter is used in two different reaction stages for amplification. An important feature is the use of a first stand cDNA that can form a hairpin structure at its 3' end to provide a self-priming template for second strand synthesis.

Figure 2B:
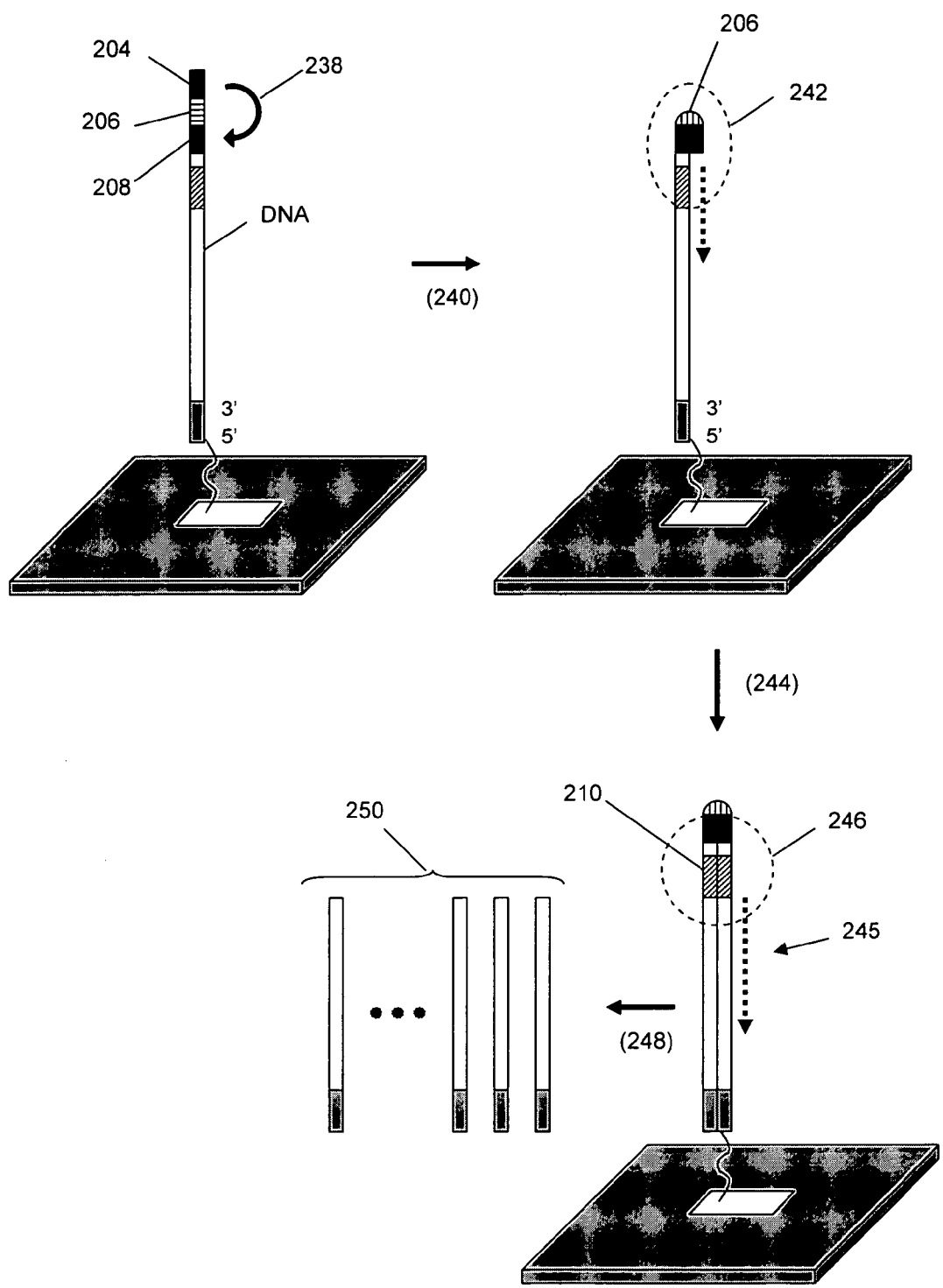

In one embodiment, such amplification is carried out in an isothermal reaction using components as illustrated in FIGS. 2A and 2B. Double stranded DNA (200) is provided having the following elements: up-stream promoter (202), first stem region (204), loop region (206), second stem region (208), promoter (210), polynucleotide (212), and primer binding site (214). Double stranded DNA (200) is treated (218) under synthesis conditions with RNA polymerase (216) that recognized up-stream promoter (202) so that RNA copies (220) are produced of the sequence downstream of up-stream promoter. Synthesis conditions depend on the particular RNA polymerase used, but usually are the manufacturer's recommended conditions, which minimally include the four ribonucleoside triphosphates and appropriate buffers. Exemplary RNA polymerases include T7 RNA polymerase, T3 RNA polymerase, SP6 RNA polymerase, and the like. RNA copies (220) are annealed by way of primer binding site (214) to primer (224) attached by its 5' end to solid phase support (226). Primer (224) and primer binding site (214) have sufficient complementarity to form a stable duplex that may be extend with a reverse transcriptase (RT), such as avian myeloblastosis virus RT, Moloney murine leukemia virus, or the like. Primer (224) may be attached to solid phase support (226) via a biotin, or equivalent capture moiety, attached to its 5' nucleotide. Alternatively, primer (226) may be directly synthesized on the surface of solid phase support (226) using 5'-phosphoramidite chemistry (e.g. Glen Research), or the like. After a stable duplex forms between primer (224) and primer binding site (214), primer (224) is treated (228) under synthesis conditions with reverse transcriptase (230) to form DNA strand (233) from RNA template (235). After such reaction is completed, RNA template (235) may be removed (236) chemically or enzymatically by conventional means, e.g. heating in sodium hydroxide solution or by RNase H treatment, after which first stem region (204) may anneal to second stem region (208) to form an extendable duplex. Such extendable duplex is treated under synthesizing conditions with DNA polymerase (242) to form (244) double stranded DNA (245), after which double stranded DNA (245) is treated under synthesis conditions with RNA polymerase that recognizes promoter (210). Such reaction (248) produces RNA transcripts (250). Optionally, RNA transcripts (250) may be converted into DNA annealing a primer to primer binding site (214) and extending the primer with a reverse transcriptase along RNA transcripts (250).

Figure 2C:
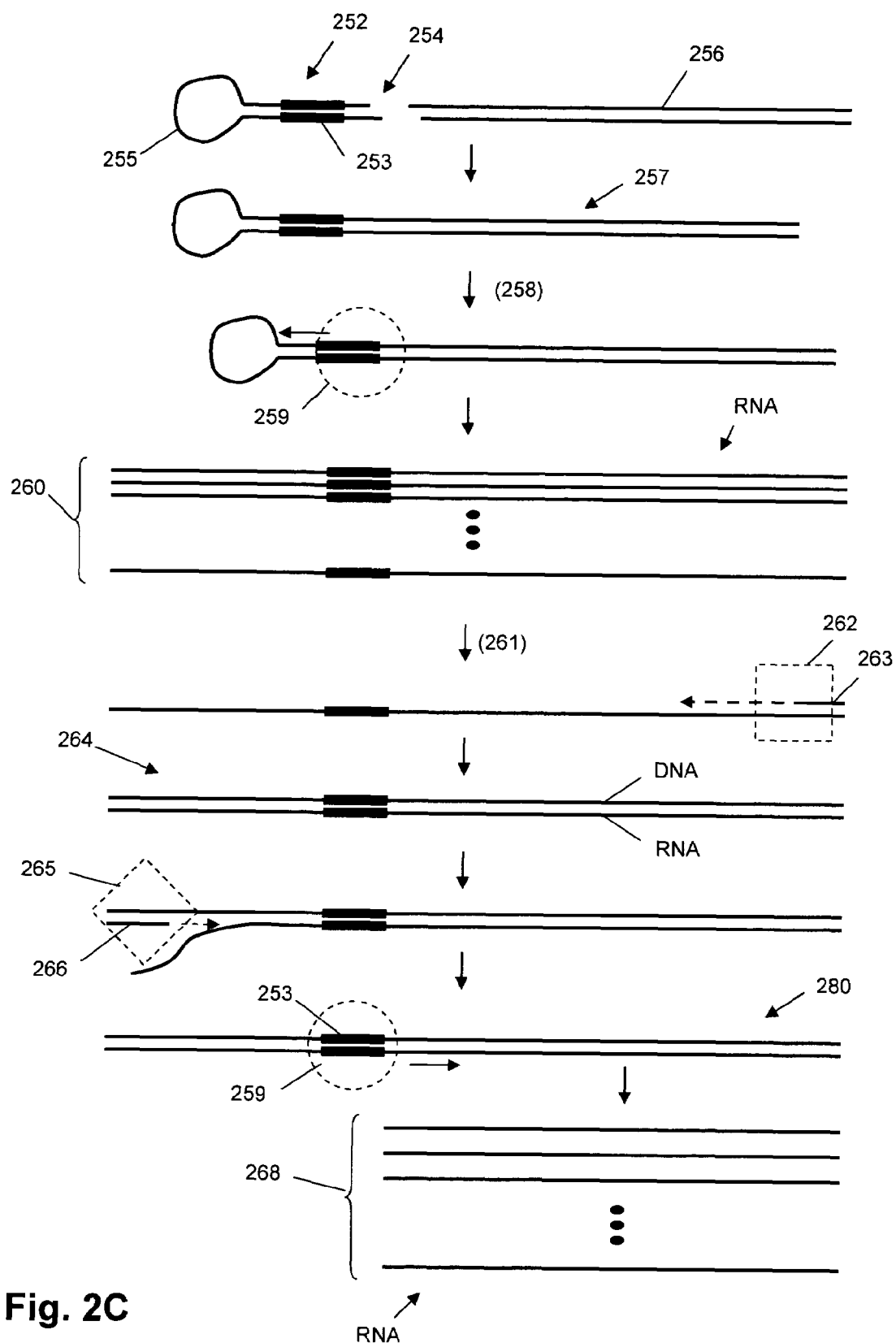
Figure 2D:
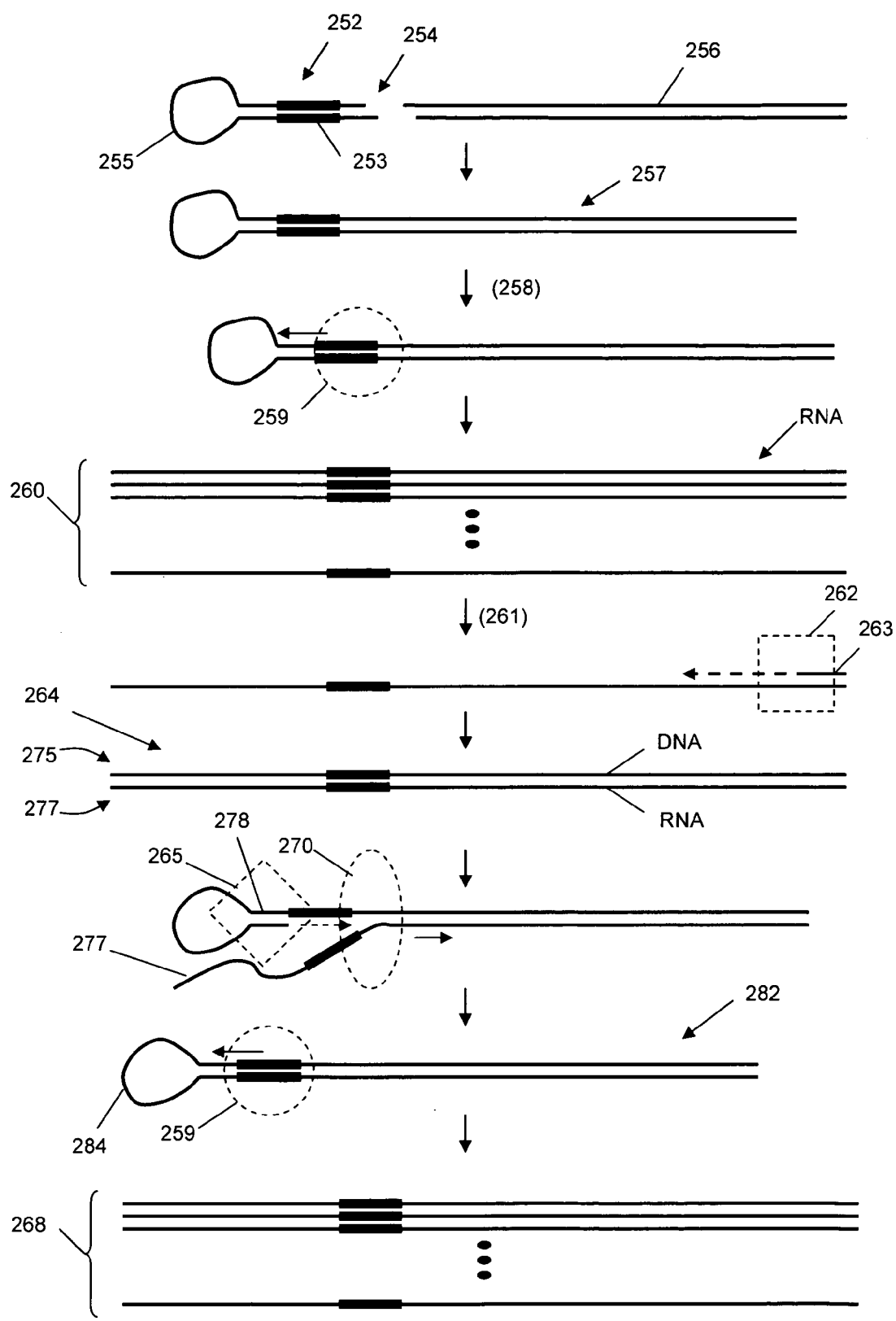

In another embodiment, the method of the invention is implemented using a single promoter sequence by reversing its orientation relative to that of the previous embodiment and ligating a hairpin adaptor containing it to the polynucleotide to be amplified. Part of the invention is the discovery that RNA polymerases recognizing a promoter oriented to promote synthesis in the direction of a hairpin loop are able to synthesize an RNA transcript across the loop and along the complementary strand of the promoter sequence itself. As illustrated in FIG. 2C, hairpin adaptor (252) comprising loop (255), promoter sequence (253), and, preferably overhang (254) (to facilitate ligation) is ligated to a complementary overhang on an end of polynucleotide (256). Polynucleotide (256) preferably includes a primer binding site at its end opposite to that of the hairpin adaptor (252), e.g. similar to (214) of FIG. 2A. In embodiments where multiple polynucleotides are amplified, preferably the polynucleotides all have a common primer binding site. After ligation, augmented sequence (257) is formed, which is treated (258) with RNA polymerase (259) that recognizes promoter sequence (253). Upon binding to promoter sequence (253), RNA polymerase (259) initiates synthesis of an RNA transcript along a template that includes loop (255). Such RNA transcripts accumulate at a linear rate with time to form an initial RNA amplicon (260). To the sequences in this amplicon are added first primers (263), which in the presence of reverse transcriptase (262) and the four nucleoside triphosphates are extended so that each forms a first cDNA strand as part of RNA-DNA heteroduplex (264). In one version of this embodiment, strand displacing primers (266) are added in order to primer synthesis of a second DNA strand by DNA polymerase (265). Such strand displacing primers may be made from, or contain, peptide nucleic acids, or like nucleotide analogs that are capable of forming duplexes with enhanced stability. Alternatively, the RNA strand can be digested with RNase H. After double stranded DNA (280) is formed, a second stage of RNA replication is initiated by RNA polymerase (259) at the reconstituted promoter sequence (253), which results in the generation of a secondary RNA amplicon (268). Another version of this embodiment is shown in FIG. 2D. The two versions proceed similarly up to the formation of heteroduplex (264). In the second version, ends (275) and (277) of heteroduplex (264) are unwound by helicase (270) so that stem region (278) is regenerated, thereby providing an extendable duplex. Useful helicases are described in Vincent et al, EMBO Reports, 5:795-800 (2004), and in U.S. patent publication 2004/0058378, which are incorporated by reference. Preferably, a sen1p helicase is employed in the invention, such as disclosed in Kim et al, Biochemistry, 38: 14697-14710 (1999), and Ursic et al, Nucleic Acids Research, 32: 2441-2452 (2004), both of which are incorporated by reference. The extendable duplex is extended by DNA polymerase (265) to form double stranded DNA (282) containing promoter sequence (253), which is identical to augmented sequence (257). Thus, when RNA polymerase (259) binds to promoter sequence (253) synthesis again proceeds towards loop (284) to generate secondary RNA amplicon (268).

EXAMPLE 1

Solid Phase Capture and Amplification

In this example, T7 RNA polymerase copies a template DNA to form RNA transcripts, which are captured by a unique primer and then utilized as templates to synthesize the first stranded complementary DNAs. This first strand DNA flips back at the 3' terminus to provide entry point for self-polymerization, because the 3' terminus has complementary sequence to form loop and stem structure. A T3 RNA polymerase promoter in the sequence is then reconstituted after self-polymerization. After the first in vitro transcription-reverse transcriptase (IVT-RT) mediated amplification reaction, the looped double stranded DNA serves as template in the second IVT-RT reaction to transcribe more RNA. In this embodiment, RNA is removed from the heteroduplex prior to the self-priming reaction by denaturation (i.e. in alkaline conditions or rising the temperature). Once the 3' end of cDNA is exposed as single stranded, looped double stranded DNA is synthesized on the solid surface as well as in the liquid phase by the DNA dependent DNA polymerase activity of reverse transcriptase. This looped double stranded DNA on the solid surface serves as template for IVT by T3 RNA polymerase. The transcript from T3 promoter is captured by the same capture primer. The amplification fold on the solid surface is the function of the amount of input double stranded DNA, the amount of immobilized primer to capture transcript, and the free capture primer in the second IVT-RT reaction. The amplification fold, which depends on the amount of input DNA, was estimated to be from 10 to 20000 when the second IVT-RT reaction was carried out at 37° C. for 1 to 3 hours incubation under conditions where no non-specific amplification is observed.

Structure of template for amplification. The consensus sequences of promoters T7 (Dunn and Studier (1983) J. Mol. Biol., 166: 477-535) and T3 (Beck et al (1989) J. Mol. Biol., 210: 687-701) are employed in the template to be amplified (FIG. 1A). GC pairs were placed at −18 and −19 position of T7 promoter sequence to minimize separation or "breathing" of the T7 promoter sequence at the end. The T7 leader sequence was changed from GGGAGA to GGGATT to introduce a loop and stem structure at the 3' end of first strand cDNA. Two restriction enzymes NcoI and NheI sites were located just after the T3 promoter leader sequence to permit library construction and amplification of the sequences. A tag sequence can be located after the NheI site to identify each insert fragment. Because of the difficulty in synthesizing long oligonucleotides, the length of tag sequence was reduced from five words to one word. This shorter version of template DNA was used. An 11-mer sequence was placed at the very end of the right hand side of the template for primer annealing site to permit cDNA synthesis using a reverse transcriptase. This same sequence was used for immobilize cDNA on the solid surface.

The first stranded DNA synthesis and IVT conditions. The first stranded DNA synthesis and in vitro transcription reactions were combined in one reaction. Reverse transcriptase requires potassium ion, which inhibits RNA polymerase activity when it is used in excess. On the other hand, RNA polymerase requires spermidine, which inhibits reverse transcriptase activity when it is used in excess. 2 mM spermidine and 50 mM KCl were used to facilitate both activities in one reaction. The IVT-RT reaction was performed in 20 μl reaction volume containing 50 mM KCl, 40 mM Tris-HCl (pH 8), 16 mM MgCl2, 10 mM DTT, 2 mM spermidine and 0.1 mg/ml BSA supplied with 1 mM dNTPs, 2 mM rNTPs, 0.1 pmol of template double stranded DNA and 1 μM 5' labeled fluorescent primer with Bodipy630/650 which anneals to the 3' terminus of transcript, along with RNase inhibitor, 0.5 U/μl T7 RNA polymerase and 5 U/μl Superscript II reverse transcriptase. The same fluorescent primer was used in all of experiments of this example. The IVT-RT reaction mixture was incubated at 37° C. for four hours. After incubation, aliquot was taken and mixed with blue dextran denaturing dye, denatured at 100° C. for 5 minutes and analyzed on 8% PAGE denaturing urea gel, which was run at 40 W constant for 35 min. Storm860 was used to visualize gel image and analyzed it with ImageQuant NT software.

Liquid phase amplification. The RNA-DNA heteroduplex obtained above was denatured by rising the temperature to 100 degree for 5 min to expose the single stranded 3' end of the cDNA strand for self polymerization. This enabled synthesis of the template for the IVT reaction and reverse transcription reaction simultaneously. The second IVT-RT reaction was performed under the same conditions except that instead of T7 RNA polymerase, T3 RNA polymerase was used. The second IVT-RT reaction contains 50 mM KCl, 40 mM Tris-HCl (pH 8), 16 mM MgCl2, 10 mM DTT, 2 mM spermidine and 0.1 mg/ml BSA supplied with 1 mM dNTPs, 2 mM rNTPs, an aliquot of looped single stranded DNA and 1 μM 5' labeled fluorescent primer which anneals to the 3' terminus of transcript along with RNase inhibitor, 0.5 U/μl T3 RNA polymerase and 5 U/μl Superscript II reverse transcriptase in a 20 μL reaction volume. This IVT-RT reaction mixture was incubated at 37° C. for one hour.

Solid phase amplification. A Streptavidin coated polystyrene plate (Reacti-Bind Streptavidin High Binding Capacity Coated Plates, PIERCE) was used as a solid support to immobilize biotinylated primer to capture transcripts from T7 promoter in the first IVT-RT reaction. 200 pmol of primer in 100 μl 1× BW buffer (5 mM Tris-HCl (pH 7.5), 1 mM EDTA, 1.0 M NaCl) was used for coating the plate well with biotinylated primer at room temperature for one hour incubation. After binding primer on the wells, wells were washed two times with 1× BW buffer, once with water, once with T7' buffer (40 mM Tris-HCl (pH 8), 6 mM MgCl2) prior to the first IVT-RT reaction. The IVT-RT reaction was performed in 40 μL reaction volume containing 50 mM KCl, 40 mM Tris-HCl (pH 8), 16 mM MgCl2, 10 mM DTT, 2 mM spermidine, 1 mg/ml heparin and 0.1 mg/ml BSA supplied with 1 mM dNTPs, 2 mM rNTPs, various amount of template double stranded DNA along with RNase inhibitor, 0.5 U/μl T7 RNA polymerase and 5 U/μl Superscript II reverse transcriptase. This IVT-RT reaction mixture was incubated at 37° C. for four hours. After four hours incubation, wells were washed with 1× T7' buffer two times, once with water, then RNA striping solution (0.5 M NaOH, 1.5 M NaCl) was added to the wells and incubated at room temperature for 10 to 15 min. Wells were washed with once with water, neutralized with 1 M Tris-HCl (pH 7.0) two times, washed with water once, washed with 10 mM Tris-HCl (pH 8.0) once and then 1× T7' buffer two times prior to the second IVT-RT reactions. The second IVT-RT reaction was performed in 40 µl reaction volume containing 50 mM KCl, 40 mM Tris-HCl (pH 8), 16 mM MgCl2, 10 mM DTT, 2 mM spermidine and 0.1 mg/ml BSA supplied with 1 mM dNTPs, 2 mM rNTPs and 1 µM 5' labeled fluorescent primer along with RNase inhibitor, 0.5 U/µL T3 RNA polymerase and 5 U/µl Superscript II reverse transcriptase. The reactions were incubated at 37° C. and 1 µL aliquots were drown from the reactions at appropriate time and mixed with 3 µL of blue dextran denaturing dye, denature at 100 deg for 5 min prior to apply samples on 8% Polyacrylamide gel (FIG. 4).

Estimation of amplification fold on the solid surface. The amount of final amplified DNA in the polystyrene well was estimated by the consumption of the fluorescent labeled oligonucleotide. The total capture oligonucleotide used in the reaction is 40 pmol in 40 µl second IVT-RT reaction volume. The final amount of amplified DNA is totally dependent on the amount of this capture oligo. Various amounts of input DNA (0.001 pmol to 1 pmol) were used in the first IVT-RT reaction. The incubation time for the first IVT-RT reaction was fixed at four hours. After removing RNA from first stranded DNA attached to the polystyrene surface, second IVT-RT cocktails were added to each well and 1 µL reactions were carried out. Samples were denatured with blue dextran denaturing dye and analyzed on 8% PAGE denaturing gel. The signal intensity was quantified by ImageQuantNT. As 1 µl sample at T=0 shows the initial amount of capture oligo, which is 1 pmol, the amounts of amplified cDNA (Dout) is estimated by Dout=IcDNA/(IcDNA+Icap)×1 pmol, where IcDNA is the signal intensity of amplified cDNA and Icap is the signal intensity of unincorporated capture oligonucleotide. The amplification fold is defined by Dout/Din. Dout and Din are the total amount of estimated output DNA and input DNA, respectively.

Figure 3:
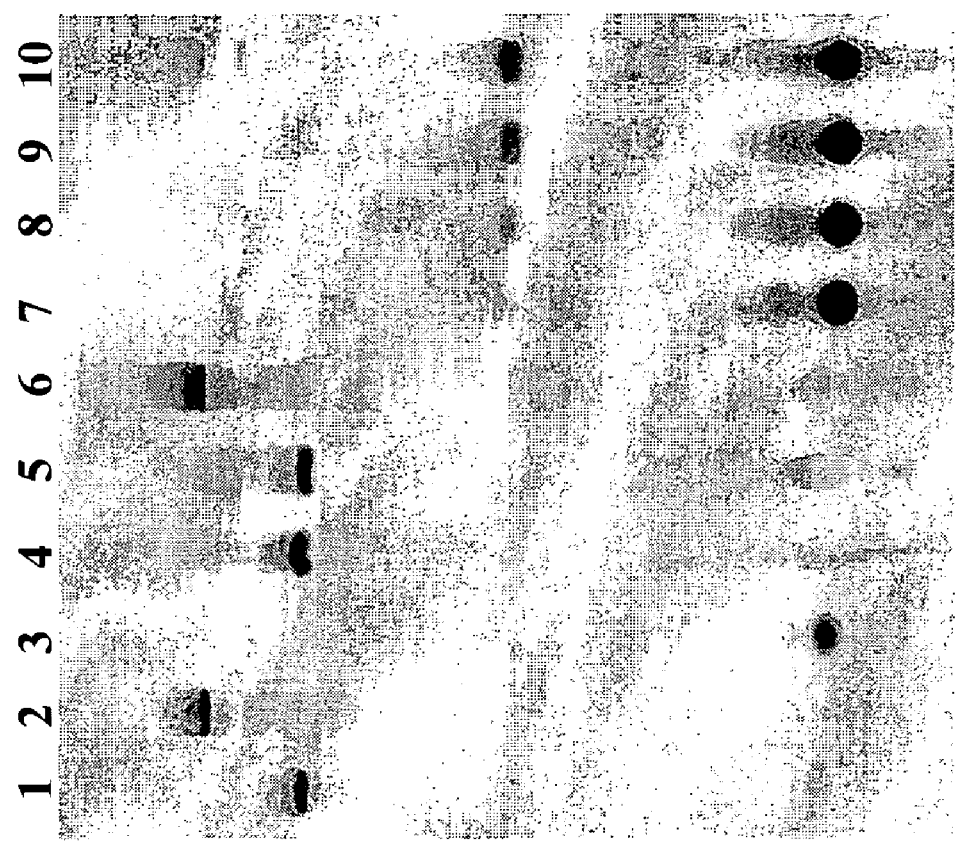
FIG. 3 shows images of gel lanes containing fragments from different steps of one embodiment of the method of the invention.

Displacement of the looped RNA structure at its 5' terminus by reverse transcriptase. Full length cDNA synthesis was carried out, as the amplification scheme requires formation of a hairpin at the 3' end of the first stranded cDNA for providing self priming to regenerate a double stranded DNA. FIG. 3 (lane 4 and lane 5) shows the position of the reverse transcribed first stranded cDNA from IVT-RT reaction compared with the size of the chemically synthesized full-length cDNA (FIG. 3 lane 1). The size of this chemically synthesized oligonucleotide is 72 nucleotides and that of the first stranded cDNA is expected to be 72 nucleotides (FIG. 1). The band size on lane 4 and 5 indicate that the full-length cDNA is synthesized. Although the 5' terminus of transcript has looped structure, this structure is unfolded and stretched to serve as a template to make full-length cDNA.

Removing RNA from heteroduplex to give looped DNA with 3' end for the entry point of DNA polymerase and reconstitution of an active T3 promoter. Although the looped structure of transcript at its 5' terminus is stretched, or linearized, by reverse transcriptase (FIG. 3 lane 4 and lane 5), the heteroduplex is sufficiently stable to prevent the formation of looped cDNA at its 3' end. The size of the first stranded cDNA is not elongated more than the size of its full-length cDNA in the IVT-RT reaction. RGTP was substituted with rITP to reduce the hydrogen bonding in the heteroduplex; however, no looped double stranded DNA was observed. Since the synthesized single stranded DNA, which contains looped structure at its 3' terminus, is able to utilize the looped 3' terminus as an entry point for polymerization by self priming (FIG. 3 lane 2), single stranded cDNA striped off from the RNA-DNA heteroduplex can be self primed. Therefore, RNA was removed from heteroduplex by RNaseH treatment followed by heat denaturation in the liquid phase amplification or alkaline denaturation in the solid phase amplification. After such treatment, the single stranded synthesized DNA was capable to provide 3' priming point by self-annealing at its 3' terminus (FIG. 3 lane 6). Once the RNA was removed from the heteroduplex, single stranded DNA self primed and was copied by Klenow(exo-) DNA polymerase and/or SSII. This looped double stranded DNA reconstitute an active T3 promoter from which a transcript of the expected size was produced (FIG. 3 lane 8 to lane 10). Although the reaction run on lane 7 did not contain T7RNA polymerase and SSII in the first IVT-RT reaction (FIG. 3 lane 3), a weak signal was observed on lane 7. This weak signal was derived from the initial input double stranded DNA carried over to the second IVT-RT reaction. Thus, the labeled DNA on lane 8 to lane 10 migrated at the same position at which the weak band is observed on lane 7. This indicates that the size of transcripts were the same, as they were transcribed from the same T3 promoter.

Figure 4A:
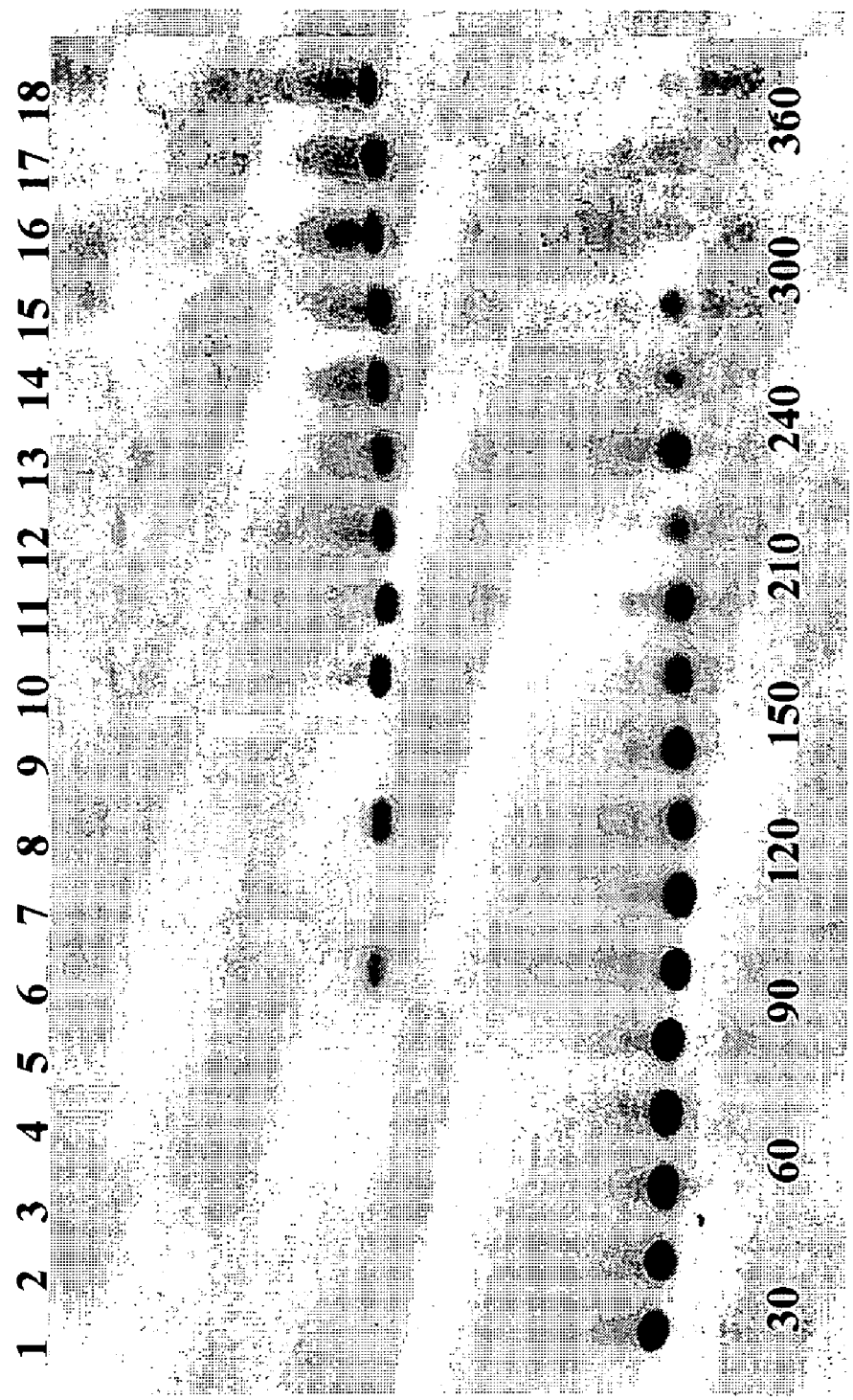
FIGS. 4A and 4B show images of gel lanes containing product fragments from amplification reactions of the invention carried out for different reaction times in one embodiment of the invention.
Figure 4B:
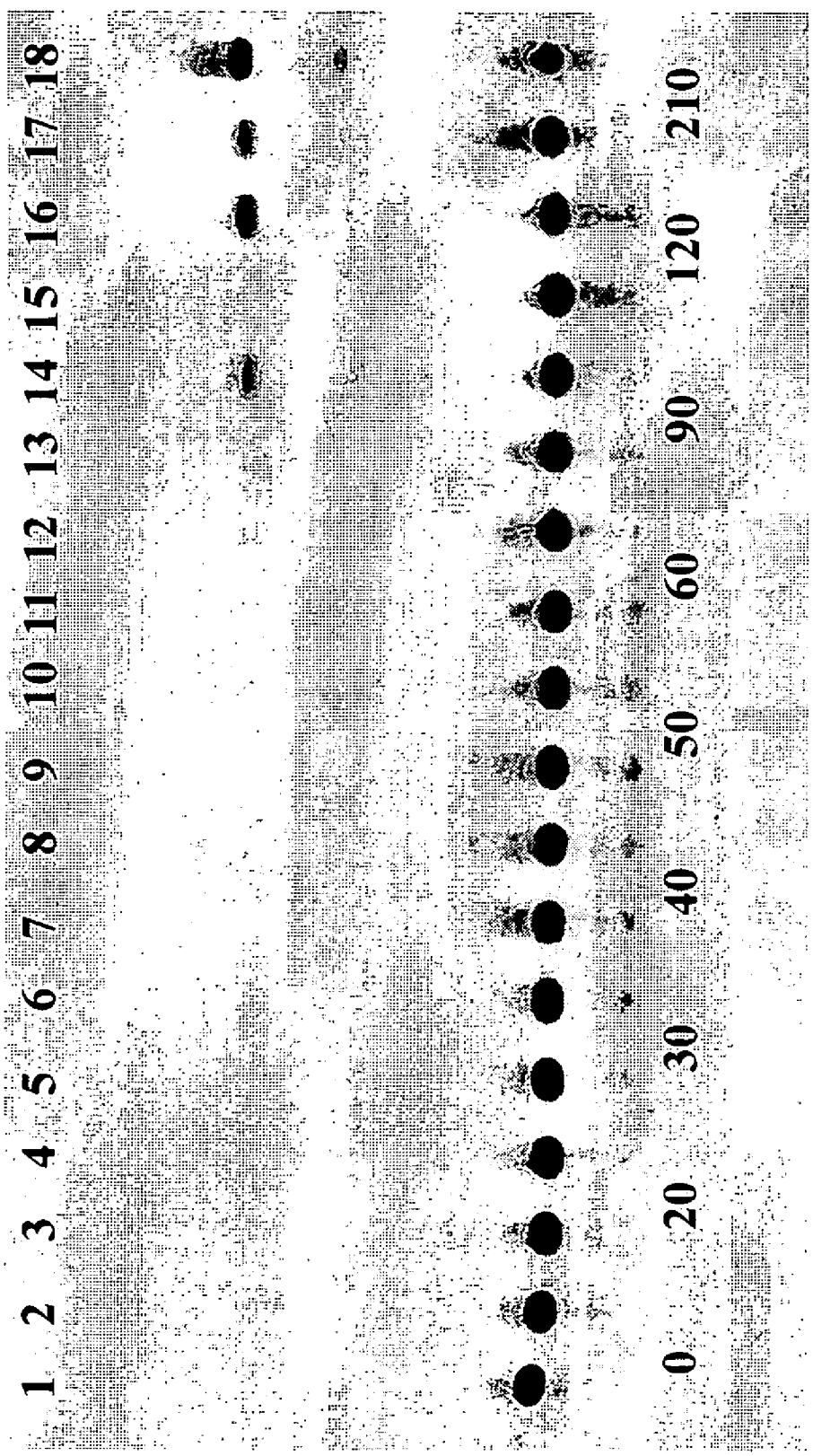

Degree of amplification on the solid surface. The prolonged incubation time in the second IVT-RT reaction leads to the consumption of the free capture primers in the capture primer uncoated well (FIGS. 4A and 4B). When there is no capture primer in the well, looped double stranded DNA cannot be synthesized (FIG. 1B). Background cDNA synthesis in the second IVT-RT reaction is due to the non-specific binding of the initial input DNA to the well in the first IVT-RT reaction. There are two possible scenarios can be considered for this non-specific amplification. The first one is non-specific bond DNA on the well is carried over to the second IVT-RT reaction and the second one is that transcript is carried over and served as the template for cDNA synthesis in the second IVT-RT reaction. However, the second case is very unlikely because of the following reasons. If the T7 transcripts is carried over after denaturation process to the second IVT-RT reaction and this transcript is utilized to synthesize cDNA, T3 promoter is still inactive because heteroduplex is too stable to give 3' self priming site. Thus it is very unlikely that the T7 transcript carried over is a template in the second IVT-RT reaction that caused non-specific amplification. This was confirmed by employing an initial template with an inactive T3 promoter sequence by substituting dATP with diaminopurine, which suppresses the back ground cDNA synthesis. If the back ground amplification is suppressed, more capture primer and precursors will be consumed only by the transcript derived from double stranded looped DNA, which will make the amplification fold be increased. The amplification fold was estimated for each input DNA at the maximal incubation time which does not cause any back ground amplification. The less the input DNA is used, the higher the amplification fold was observed (table 1). The amount of final amplified cDNA was restricted to the total amount of free capture primer in the second IVT-RT reaction, which is 40 pmol in the experiments. As no more than 40 pmol of cDNA synthesis can be expected, the maximal amplification is 40 when 1 pmol of input DNA was used. What is more, the higher amount of input DNA increased the back ground amplification before the IVT reaction achieved saturation state. Thus, the less input DNA gives higher amplification fold. Although, the minimal amount of input DNA used was 25 amol/µl, it can be decreed further, in which case a higher amplification fold more than 20,000 can be expected.

Figure 5:
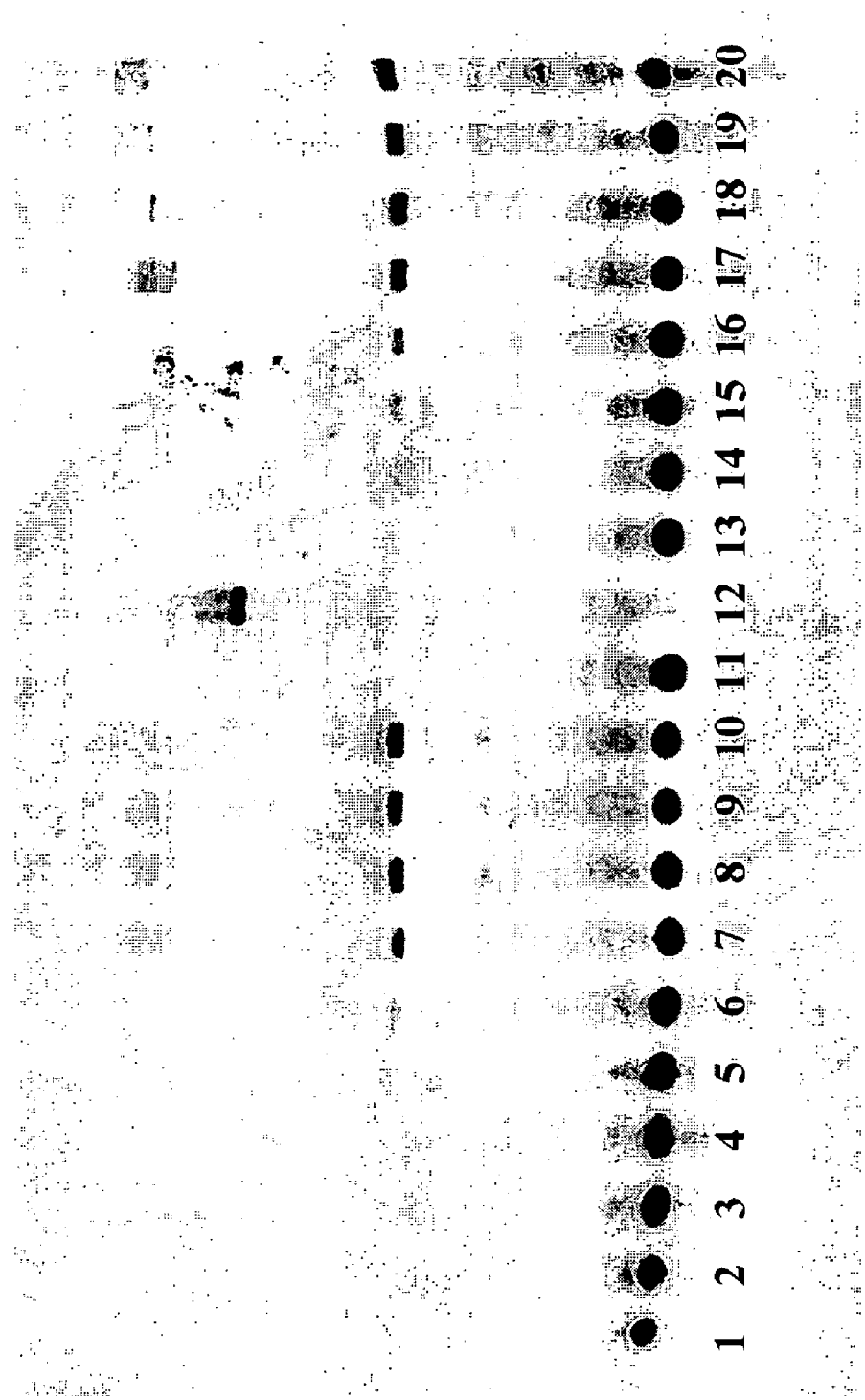
FIG. 5 shows images of gel lanes containing products of reactions with Klenow (exo-) DNA polymerase on the amplification reaction in one embodiment of the invention.

The effect of Klenow (exo-) DNA polymerase in the amplification reaction. FIG. 5 shows the effect of using Klenow (exo-) DNA polymerase in the liquid phase amplification reaction. The first IVT-RT reaction was performed at 37° C. for 4 hours followed by second IVT-RT reaction for one hour. In the absence of T7RNA polymerase and RT in the first IVT-RT reaction, 1 pmol template was required to see a weak signal in the second IVT-RT reaction in the absence of Klenow (exo-) DNA polymerase (FIG. 5 lane 6). In the presence of T7RNA polymerase and RT in the first IVT-RT reaction, minimal amount of the template to be detected after amplification is 0.01 pmol (FIG. 5 lane 14). The addition of Klenow (exo-) DNA polymerase to the second IVT-RT reaction increased the amount of amplified product (FIG. 5 lane 7 to lane 10 and lane 17 to lane 20). This might be because the polymerization efficiency of Klenow (exo-) DNA polymerase is higher than that of RT, which enables the production of more looped double stranded DNA in the second IVT-RT reaction (FIG. 5 lane 13 to lane 20). However, this enhancement was also observed under the conditions when no first stranded DNA was synthesized (lane 7 to 10). The first IVT-RT reaction did not show any significant effect on the amplification fold in the second IVT-RT reaction in the presence of Klenow (exo-) DNA polymerase. Even 0.001 pmol of template in the absence of T7RNA polymerase and RT showed the amplified product (FIG. 5 lane 7). The size of these products on lane 7 to lane 10 indicates that they are obtained from RNA transcribed from the T3 promoter on the initial DNA as a template. Thus, the effect of enhancement of Klenow (exo-) DNA polymerase is mainly on the first stranded cDNA synthesis from the T3 transcript as a template. The enhancement of final product by Klenow (exo-) DNA polymerase probably due to the rapid and recurrent entry of the primer to the annealing site on the T3 transcript by the strand displacement activity of Klenow (exo-) DNA polymerase rather than efficient polymerization activity.

Although DNA dependent DNA polymerase activity of reverse transcriptase was used for preparing template in the second IVT-RT reaction, an increase in the amplification fold might be accomplished by employing the strand displacement activity of Klenow (exo-) DNA polymerase in the IVT-RT reaction for the template DNA lacking active T3 promoter.

Double stranded DNA can be amplified isothermnically by the combination of IVT and RT reactions. Transcript from the T7 promoter is primed and served as a template to synthesize full length cDNA. Although, 5' end of transcript has a stem and loop structure which potentially can truncate cDNA synthesis, the reverse transcriptase displace the 5' looped RNA structure and copied it to the end of the template strand. Preferably RNA is removed from the heteroduplex to permit formation of the 3' looped DNA structure, otherwise the heteroduplex is too stable to permit the formation of a 3' stem and loop structure for self priming. Once RNA is removed, the remaining sequence self primed efficiently and RT elongate the priming site to the end to reconstitute the T3 promoter. This looped double stranded DNA served as a template for the second IVT reaction. The input double stranded DNA is amplified as anti-sense single stranded DNA.

FIG. 1 Structure of the template sequence to be amplified. (A. Input DNA) T7 and T3 promoter sequences are shown in bold. Stem and loop structure are between these two promoter sequences. Stem region is underlined and loop region is represented in small letters. After T3 promoter leader sequence, NocI and NheI sites are located, which are indicated in italicized small letters. The sequence for annealing capture primer is shown in bold lowercase on the right. (B. pT7 Transcript) The transcript from T7 promoter is shown. 5' end stem and loop structures are underlined and in small letters, respectively. The size of full-length cDNA (C) is 72 mer, and that of looped double stranded DNA (D) is 131-mer.

FIG. 2 Amplification steps. Din and Dout represent the input double stranded DNA and the output single stranded DNA, which is the anti-sense strand of the input DNA. R7 is the transcript from T7 promoter, which anneals to the immobilized capture primer (Cimm) on the solid surface. 5' end of Cimm is attached to the solid surface. R7Dc is heteroduplex form between T7 transcript and the full-length cDNA. Dc is the single stranded full-length cDNA attached to the solid surface after R7 is removed. Dloop is the looped double stranded DNA, which serves as template for IVT by T3 RNA polymerase to transcribe R3. R3 is annealed with free capture primer (Cfree) in the solution and form R3Cfree. Cfree 3' end is extended by RT to form heteroduplex R3Dout.

FIG. 3 First and second IVT-RT reaction. The transcript in the first IVT-RT reaction was annealed to the fluorescent labeled capture primer. Reverse transcription reaction and second IVT reactions were performed in the liquid phase. First lane shows the position of the chemically synthesized 72 mer DNA, and the second lane shows the position of the looped double stranded DNA, whose size is 131-mer, synthesized from the same DNA run on the first lane by Klenow (exo-) DNA polymerase. Lane 3 to lane 6 shows the first IVT-RT reactions with different enzyme combinations. The reaction run on lane 3 did not contain any enzymes. The reaction on lane 4 contains T7 RNA polymerase and SSII, the reaction on lane 5 and lane 6 contains T7 RNA polymerase, SSII and RNaseH. All the reactions were heat denatured. The reaction run on lane 6 was followed by polymerization with Klenow (exo-) DNA polymerase after heat denaturation. Aliquots were taken from the reactions run on lane 4 to lane 6 and added to the second IVT-RT reaction, each aliquots from second IVT-RT reactions were run on from lane 7 to lane 10, respectively.

FIG. 4 Time course of amplification reaction. The Streptavidin coated polystyrene plate were charged with (lanes in even number) or without (lanes in odd number) capture primer. After first IVT-RT reactions in the well, wells were washed and second IVT-RT reaction mixtures were added to each well. 1 µl of aliquots of reactions were drown from each well at indicated time (in min) shown on the bottom of each lane. The total amount of input DNA used in the first IVT-RT reaction was 0.01 pmol in (A) and 0.1 pmol in (B), respectively.

FIG. 5 The effect of Klenow (exo-) DNA polymerase in the amplification reaction. Lane 1 to 10 shows the reaction in the absence of T7 RNA polymerase and RT in the first IVT-RT reaction. The reactions on lane I and lane 2 did not contain T3 RNA polymerase nor RT. Lane 3 to lane 10 shows the reaction in the presence of T3 RNA polymerase and RT in the second IVT-RT reaction. Klenow (exo-) DNA polymerase was added to the reactions shown on lane 7 to lane 10 along with T3 RNA polymerase and RT. Lane 11 to lane 20 shows the reaction in the presence of T7 RNA polymerase and RT in the first IVT-RT reaction. The reaction on lane 11 and lane 12 did not contain T3 RNA polymerase nor RT. Lane 13 to lane 20 shows the reaction in the presence of T3 RNA polymerase and RT in the second IVT-RT reaction. Klenow (exo-) DNA polymerase was added to the reactions shown on lane 17 to lane 20 along with T3 RNA polymerase and RT. The band observed on lane 12 is the full-length first stranded DNA. The total amount of template used in the 20 µl reaction is as follows: lane 1 and 11, 1 fmol, lane 2 and 12, 1 pmol, lane 3, 7, 13 and 17, 0.001 pmol, lane 4, 8, 14 and 18, 0.01 pmol, lane 5, 9, 15 and 19, 0.1 pmol, lane 6, 10, 16 and 20, 1 pmol, respectively.

Table 1 Amplification fold on the solid surface. The amplification fold was estimated at the maximum incubation time Tmax when back ground amplification (odd lanes on FIGS. 4A and B) was not observed. The total amount of input template DNA (Din) and the estimated total amount of output DNA (DNAout) are shown on the table.

EXAMPLE 2

Amplification with a Single RNA Polymerase

Figure 6:
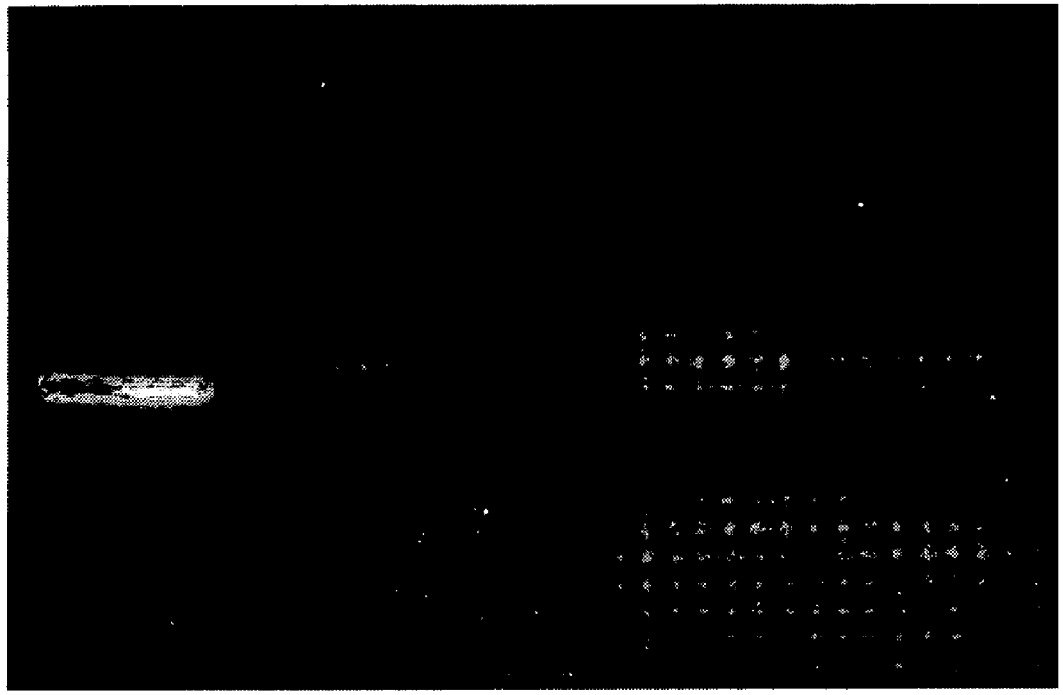
FIG. 6 shows an image of gel lanes containing reaction components from an analysis of the reaction showing that T7 RNA polymerase can transcribe through a loop of a hairpin adaptor.

In this example, a hairpin adaptor containing a single promoter site was ligated to an end of the polynucleotide to be amplified (thereby forming an augmented sequence). The promoter was oriented in the hairpin adaptor so that transcription takes place in the direction of the loop, thereby creating transcripts containing a copy of the loop, a single strand of the promoter, and the polynucleotide. The sequence of the hairpin adaptor (R6) is as follows (SEQ ID NO: 5):

5'-pATCCCTTGCT[pT7]GGGAGACCCTATCTTAGGGTCTCCC[pT7']AGCAAGG where p is a phosphate group, [pT7] is the T7 promoter sequence, and [pT7'] is the complement of the T7 promoter sequence, the double underlined nucleotides are the loop region, and the first G of the single underlined nucleotides is the first copied nucleotide of a T7-generated transcript. After ligation, the augmented sequence was transcribed with T7 RNA polymerase under conventional reaction conditions to generate RNA transcripts. The reaction components were analyzed by gel electrophoresis, the image of which is shown in FIG. 6. Lane 1 contains the polynucleotide to be amplified before ligation with the hairpin adaptor. Lane 2 contains the product of the ligation reaction where the hairpin adaptor was ligated to the polynucleotide to form the augmented sequence. Lane 3 shows the same product after DNase I treatment. Lane 4 contains the IVT reaction product formed by treating the product of lane 2 with T7 RNA polymerase. Lane 5 contains the same product of lane 4 after DNase I treatment. Lane 4 show that full length transcription through the loop was achieved.

The above teachings are intended to illustrate the invention and do not by their details limit the scope of the claims of the invention. While preferred illustrative embodiments of the present invention are described, it will be apparent to one skilled in the art that various changes and modifications may be made therein without departing from the invention, and it is intended in the appended claims to cover all such changes and modifications that fall within the true spirit and scope of the invention.

TABLE 1

| DNAin (pmol) | Tmax (min) | DNAout (pmol) | Amp Fold |
| --- | --- | --- | --- |
| 0.001 | 200 | 20.8 | 20800 |
| 0.010 | 150 | 16.8 | 1680 |
| 0.100 | 120 | 12.5 | 125 |
| 1.000 | 60 | 10.5 | 10.5 |

We claim:

1. A method of replicating a polynucleotide sequence, the method comprising the steps of:
   providing a double stranded DNA having a hairpin at one end, the polynucleotide sequence at the other end, and disposed therebetween a promoter sequence oriented so that synthesis by an RNA polymerase recognizing the promoter sequence proceeds in the direction of the hairpin;
   transcribing the double stranded DNA with an RNA polymerase that recognizes the promoter sequence to form an RNA transcript comprising copies of the promoter sequence and the polynucleotide sequence;
   generating a complementary DNA from the RNA transcript;
   displacing a 5' end of the RNA transcript from the complementary DNA so that the hairpin is reconstituted; and
   extending the hairpin to generate double stranded DNA, wherein the generated double stranded DNA contains the reconstituted hairpin, a reconstituted promoter sequence and the polynucleotide sequence, thereby replicating the polynucleotide sequence.

2. The method of claim 1 wherein said step of generating includes forming a heteroduplex of said complementary DNA and said RNA transcript and wherein said step of displacing includes treating the heteroduplex with a helicase.

3. The method of claim 1 wherein said loop region contains from three to six nucleotides.

4. The method of claim 1 wherein said polynucleotide sequence comprises a primer binding site at the end opposite to that of said hairpin adaptor, wherein a first primer specific for said primer binding site is used in generating said complementary DNA.

5. The method of claim 4 wherein said method is a method for amplifying multiple polynucleotide sequences, and wherein each of said multiple polynucleotide sequences comprises said primer binding site specific for said first primer.

6. The method of claim 1 wherein said providing step comprises ligating an adaptor to said polynucleotide sequence, wherein said adaptor comprises said hairpin and said promoter sequence.

7. The method of claim 1 wherein said RNA polymerase is selected from the group consisting of: T7 RNA polymerase, T3 RNA polymerase and SP6 RNA polymerase.

8. The method of claim 2 wherein said helicase is sen1 p helicase.

9. The method of claim 1 wherein said RNA polymerase recognizes the reconstituted promoter sequence in said generated double stranded DNA and synthesizes RNA transcripts.

10. A method of replicating a polynucleotide sequence, the method comprising the steps of:
    providing a double stranded DNA having a hairpin at one end, the polynucleotide sequence at the other end, and disposed therebetween a promoter sequence oriented so that synthesis by an RNA polymerase recognizing the promoter sequence proceeds in the direction of the hairpin;

transcribing the double stranded DNA with an RNA polymerase that recognizes the promoter sequence to form an RNA transcript comprising copies of the promoter sequence and the polynucleotide sequence, thereby replicating the polynucleotide sequence.

11. The method of claim 10 wherein said method further comprises generating a complementary DNA from the RNA transcript.

12. The method of claim 11 wherein said polynucleotide sequence comprises a primer binding site at the end opposite to that of said hairpin adaptor, wherein a first primer specific for said primer binding site is used in generating said complementary DNA.

13. The method of claim 12 wherein said method is a method for amplifying multiple polynucleotide sequences, and wherein each of said multiple polynucleotide sequences comprises said primer binding site specific for said first primer.

14. The method of claim 10 wherein said loop region contains from three to six nucleotides.

15. The method of claim 10 wherein said providing step comprises ligating an adaptor to said polynucleotide sequence, wherein said adaptor comprises said hairpin and said promoter sequence.

16. The method of claim 10 wherein said RNA polymerase is selected from the group consisting of: T7 RNA polymerase, T3 RNA polymerase and SP6 RNA polymerase.

* * * * *

UNITED STATES PATENT AND TRADEMARK OFFICE
CERTIFICATE OF CORRECTION

PATENT NO.        : 7,579,153 B2
APPLICATION NO.   : 11/338533
DATED             : August 25, 2009
INVENTOR(S)       : Brenner et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 513 days.

Signed and Sealed this

Fourteenth Day of September, 2010

David J. Kappos
*Director of the United States Patent and Trademark Office*

SEQUENCE LISTING

```
<160> NUMBER OF SEQ ID NOS: 5

<210> SEQ ID NO 1
<211> LENGTH: 91
<212> TYPE: DNA
<213> ORGANISM: Unknown
<220> FEATURE:
<223> OTHER INFORMATION: probe
<220> FEATURE:
<221> NAME/KEY: promoter
<222> LOCATION: (3)..(19)
<220> FEATURE:
<221> NAME/KEY: promoter
<222> LOCATION: (33)..(59)

<400> SEQUENCE: 1
gctaatacga ctcactatag ggattctatc ccaattaacc ctcactaaag ggagaccatg    60
gtcttgctag ccttgaaccg tcgattggct t                                   91

<210> SEQ ID NO 2
<211> LENGTH: 72
<212> TYPE: RNA
<213> ORGANISM: Unknown
<220> FEATURE:
<223> OTHER INFORMATION: probe

<400> SEQUENCE: 2
gggauucuau cccaauuaac ccucacuaaa gggagaccau ggucuugcua gccuugaacc    60
gucgauuggc uu                                                        72

<210> SEQ ID NO 3
<211> LENGTH: 72
<212> TYPE: DNA
<213> ORGANISM: Unknown
<220> FEATURE:
<223> OTHER INFORMATION: probe
```

-continued

```
<400> SEQUENCE: 3
aagccaatcg acggttcaag gctagcaaga ccatggtctc cctttagtga gggttaattg    60
ggatagaatc cc                                                       72

<210> SEQ ID NO 4
<211> LENGTH: 65
<212> TYPE: DNA
<213> ORGANISM: Unknown
<220> FEATURE:
<223> OTHER INFORMATION: probe
<220> FEATURE:
<221> NAME/KEY: promoter
<222> LOCATION: (43)..(59)

<400> SEQUENCE: 4
aagccaatcg acggttcaag gctagcaaga ccatggtctc cctttagtga gggttaattg    60
ggata                                                               65

<210> SEQ ID NO 5
<211> LENGTH: 76
<212> TYPE: DNA
<213> ORGANISM: Unknown
<220> FEATURE:
<223> OTHER INFORMATION: adaptor
<220> FEATURE:
<221> NAME/KEY: promoter
<222> LOCATION: (11)..(27)
<220> FEATURE:
<221> NAME/KEY: promoter
<222> LOCATION: (58)..(74)

<400> SEQUENCE: 5
atcccttgct taatacgact cactataggg agaccctatc ttagggtctc cctatagtga    60
gtcgtattaa gcaagg                                                   76
```